(12) United States Patent
Richards et al.

(10) Patent No.: US 9,833,471 B1
(45) Date of Patent: Dec. 5, 2017

(54) HYPOCHLOROUS ACID-BASED HAND SANITIZER

(71) Applicant: Reoxcyn Discoveries Group, Inc., Salt Lake City, UT (US)

(72) Inventors: Kurt Richards, Herriman, UT (US); Andrew Hoover, Pleasant Grove, UT (US)

(73) Assignee: Reoxcyn Discoveries Group, Inc., Salt Lake City, UT (US)

( * ) Notice: Subject to any disclaimer, the term of this patent is extended or adjusted under 35 U.S.C. 154(b) by 0 days.

(21) Appl. No.: 15/421,772

(22) Filed: Feb. 1, 2017

Related U.S. Application Data

(60) Provisional application No. 62/394,983, filed on Sep. 15, 2016.

(51) Int. Cl.
| | |
|---|---|
| A61K 33/00 | (2006.01) |
| A61K 33/20 | (2006.01) |
| A61K 47/02 | (2006.01) |
| A61K 47/34 | (2017.01) |

(52) U.S. Cl.
CPC .............. *A61K 33/20* (2013.01); *A61K 47/02* (2013.01); *A61K 47/34* (2013.01)

(58) Field of Classification Search
USPC .............................................. 424/600, 78.36
See application file for complete search history.

(56) References Cited

U.S. PATENT DOCUMENTS

| | | | |
|---|---|---|---|
| 4,956,184 A | 9/1990 | Kross | |
| 6,114,398 A | 9/2000 | Ratcliff | |
| 7,108,997 B2 | 9/2006 | Kettle | |
| 8,518,382 B2 | 8/2013 | Speronello et al. | |
| 8,673,297 B2 | 3/2014 | Speronello et al. | |
| 8,784,900 B2 | 7/2014 | Northey | |
| 9,072,793 B2 | 7/2015 | Eckert et al. | |
| 9,175,141 B2 | 11/2015 | Wray et al. | |
| 9,474,768 B1 | 10/2016 | Richards | |
| 2005/0089537 A1 | 4/2005 | Birnholz | |
| 2005/0196462 A1* | 9/2005 | Alimi ................... A61L 2/0088 424/600 |
| 2007/0172412 A1 | 7/2007 | Hratko et al. | |
| 2007/0281008 A1 | 12/2007 | Lin et al. | |
| 2008/0003171 A1 | 1/2008 | Smith et al. | |
| 2008/0008621 A1 | 1/2008 | Masahiro et al. | |
| 2009/0028811 A1 | 1/2009 | Potter | |
| 2009/0068122 A1 | 3/2009 | Shira et al. | |
| 2009/0169646 A1 | 7/2009 | Bosch et al. | |
| 2009/0258083 A1* | 10/2009 | Calderon ................ C01B 11/04 424/600 |
| 2010/0012132 A1 | 1/2010 | Harrison et al. | |
| 2010/0078331 A1* | 4/2010 | Scherson ................. C25B 1/24 205/335 |
| 2012/0046556 A1 | 2/2012 | Block | |
| 2013/0164228 A1 | 6/2013 | Stanislav et al. | |
| 2013/0168260 A1 | 7/2013 | Scherson et al. | |
| 2014/0044800 A1 | 2/2014 | Robinson | |
| 2014/0328946 A1 | 11/2014 | Northey | |
| 2014/0369953 A1* | 12/2014 | Purschwitz ............ A01N 33/12 424/78.36 |
| 2015/0017257 A1 | 1/2015 | Megumi et al. | |
| 2015/0093451 A1 | 4/2015 | Neiman | |
| 2015/0099010 A1 | 4/2015 | Hoover | |
| 2015/0118180 A1 | 4/2015 | Hoover | |
| 2015/0246131 A1 | 9/2015 | Romanoschi et al. | |
| 2015/0250704 A1 | 9/2015 | Romanoschi et al. | |

FOREIGN PATENT DOCUMENTS

| | | |
|---|---|---|
| CN | 102167997 | 6/2013 |
| EP | 1886664 | 2/2008 |
| WO | WO 9934773 | 7/1999 |
| WO | WO 2010004699 | 1/2010 |
| WO | WO 2015002932 | 3/2015 |

OTHER PUBLICATIONS

Chen, "Novel technologies for the prevention and treatment of dental caries: a patent survey", Expert Opin Ther Pat. May 2010; 20(5): 681-694.

Prasanth, "Antimicrobial Efficacy of Different Toothpastes and Mouthrinses: An In Vitro Study", Dent Res J (Isfahan), 2011 Spring, 8(2); 85-94.

"High purity, activated HCIO Perfect Perio", http://amanodental.com/english/PerfectPerio-how-to-use.pdf, Nov. 2010.

* cited by examiner

*Primary Examiner* — Walter Webb
(74) *Attorney, Agent, or Firm* — Knobbe Martens Olson & Bear LLP

(57) ABSTRACT

A sanitizing formulation is disclosed for use as a hand sanitizer. The formulation may include hypochlorous acid, a silicone polymer or blend thereof, sodium phosphate, hydrochloric acid, and sodium magnesium silicate. Methods of using and making the sanitizing formulation are also disclosed.

11 Claims, No Drawings

HYPOCHLOROUS ACID-BASED HAND SANITIZER

RELATED APPLICATIONS

This application claims the benefit of priority to U.S. Provisional Patent Application No. 62/394,983, filed Sep. 15, 2016, the disclosure of which is incorporated by reference herein in its entirety.

FIELD OF THE DISCLOSURE

The present disclosure relates generally to sanitizer formulations and methods of use. More specifically, the present disclosure is related to hand sanitizers having hypochlorite, or acids or salts thereof, sodium magnesium silicate, and a silicone polymer or blend thereof, and methods of sanitizing hands using the formulations described herein.

BACKGROUND

Sanitizers are used in a variety of applications, including in home use, medical facilities, or industrial applications. Sanitizers are useful for their antimicrobial properties, including the ability to remove microbes from surfaces. Such microbes include, for example, bacteria, yeasts, viruses, fungi, mold, and protozoa. These microorganisms contribute to human disease. Therefore, it is desirable to remove these microorganisms from surfaces.

Many microorganisms develop a tolerance for sanitizing formulations. For example, some microorganisms have become resistant to treatments, and are responsible for serious infections in hospitals and other healthcare facilities. Such microorganisms are sometimes referred to as superbugs. These superbugs have developed resistance to standard cleaning procedures and/or resistance to many disinfectants (such as antibiotics).

A common means of removing microorganisms from a surface, such as hands, includes washing with soap. The use of soap is effective at removal of microorganisms, but requires large quantities of water to remove the soap from the surface being disinfected. Thus, in locations where water is limited or inaccessible, or where the use of water is impractical, the use of soap to disinfect a surface is undesirable or inconvenient. In addition, the frequent use of soap in the washing of hands can result in increased dryness of hands, causing discomfort and irritation.

Many sanitizing compositions contain alcohol. Alcohol is a known disinfectant that destroys microorganisms that are living on the surface of an object, such as on hands, instruments, or other surfaces. Alcohol diffuses through the bacterial cell membrane, denatures bacterial proteins, thereby destroying bacteria. The use of alcohol in disinfectants is convenient because alcohol rapidly evaporates, eliminating the use of water to remove the sanitizer from the surface or from the skin. However, alcohol-based sanitizers are difficult to clean when spilled in hospitals or in health care facility settings. Alcohol-based sanitizers also release undesirable fumes and odors that cause irritation. Furthermore, alcohol-based sanitizers can be the source of alcohol poisoning.

SUMMARY

The present disclosure describes sanitizing compositions having hypochlorite, or acids and salts thereof, a silicone polymer or a blend thereof, and sodium magnesium silicate.

Also described are methods of using the sanitizing formulations. The formulations and methods of using the formulations described herein can be used as an effective disinfectant against drug-resistant microorganisms.

Accordingly, provided herein is a sanitizing formulation. In some embodiments, the sanitizing formulation includes one or more of hypochlorite, a silicone polymer or blend thereof, a buffer, and an emulsifier.

In some embodiments is provided a formulation including one or more of a hypochlorite solution and a silicone polymer or blend thereof.

In some embodiments, the sanitizing formulation includes, for example, one or more of hypochlorous acid, sodium phosphate, sodium magnesium silicate, and a silicone polymer or blend thereof.

In some embodiments, the hypochlorous acid is present in an amount of about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, the hypochlorous acid is present in an amount of about 50 to about 200 ppm. In some embodiments, the hypochlorous acid is present in an amount of about 75 ppm.

In some embodiments, the sodium phosphate is present in an amount of about 0.05%, 0.1%, 0.2%, 0.3%, 0.4%, 0.5%, 1%, 1.5%, 2%, or 2.5% w/v or within a range defined by any two of the aforementioned amounts. In some embodiments, the sodium phosphate is present in an amount of about 0.1 to about 0.5% w/v. In some embodiments, the sodium phosphate is present in an amount of about 0.2% w/v.

In some embodiments, the sodium magnesium silicate is present in an amount of about 0.1%, 0.25%, 0.5%, 0.75%, 1%, 1.5%, 2%, 2.5%, 3%, 3.5%, 4%, 4.5%, 5%, 6%, 7%, 10%, or 15% w/v or within a range defined by any two of the aforementioned amounts. In some embodiments, the sodium magnesium silicate is present an amount of about 0 to about 5% w/v. In some embodiments, the sodium magnesium silicate is present in an amount of about 3% w/v.

In some embodiments, the silicone polymer or blend thereof is a blend of dimethicone and/or cyclomethicone. In some embodiments, the blend of dimethicone and cyclomethicone is present in an amount of about 0.5%, 1%, 1.5%, 2%, 2.5%, 3%, 3.5%, 4%, 4.5%, 5%, 10%, or 15%, w/v or within a range defined by any two of the aforementioned amounts. In some embodiments, the blend of dimethicone and cyclomethicone is present in the sanitizing formulation in an amount of about 1 to about 10% w/v. In some embodiments, the blend of dimethicone and cyclomethicone is present in an amount of about 3% w/v.

In some embodiments, the blend of dimethicone and cyclomethicone has a ratio of dimethicone to cyclomethicone of about 1:5, 1:4, 1:3, 1:2, 1:1, 2:1, 3:1, 4:1, or 5:1, or within a range defined by any two of the aforementioned ratios. In some embodiments, the ratio of dimethicone to cyclomethicone is about 1:1.

In some embodiments is provided a sanitizing formulation, including hypochlorous acid in an amount of about 75 ppm, sodium phosphate in an amount of about 0.2% w/v, sodium magnesium silicate in an amount of about 3% w/v, and a blend of dimethicone and cyclomethicone in a ratio of about 1:1 in an amount of about 3% w/v.

In some embodiments, the sanitizing formulation includes hydrochloric acid (HCl). In some embodiments, the hydrochloric acid is present in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values. In some embodiments, the HCl is present in an amount of about 0.08% w/v. In some embodiments, hydrochloric acid is added to the sanitizing formulation as a final step to adjust the pH of the formulation. In some embodiments, hydrochloric acid increases the total number of ions, and increases the viscosity of the sanitizing formulation. In some embodiments, the formulation includes hydrochloric acid or sodium phosphate. In some embodiments, the formulation includes hydrochloric acid, but not sodium phosphate. In some embodiments, the formulation includes sodium phosphate, but not hydrochloric acid.

In some embodiments, the pH of the formulation is about 5.0, 5.5, 6.0, 6.5, 6.6, 6.7, 6.8, 6.9, 7.0, 7.1, 7.2, 7.3, 7.4, 7.5, 7.6, 7.7, 7.8, 7.9, 8.0, or 8.5, or within a ranged defined by any two of the aforementioned values. In some embodiments, the pH of the formulation is in a range from about 6.5 to about 7.8.

In some embodiments, the sanitizing formulation includes water and/or buffer. In some embodiments, the water and/or buffer comprises all or substantially all of the balance of the sanitizing formulation.

In some embodiments is provided a method for disinfecting a surface. In some embodiments, the method includes applying to a surface a sanitizing formulation comprising hypochlorous acid. In some embodiments, the sanitizing formulation is as described herein. Thus, in some embodiments, the sanitizing formulation includes hypochlorous acid, sodium phosphate, sodium magnesium silicate, and a blend of dimethicone and/or cyclomethicone. In some embodiments, the sanitizing formulation includes hydrochloric acid, water, and a buffer, or combinations thereof. In some embodiments, the sanitizing formulation includes about 75 ppm hypochlorous acid, about 0.2% w/v sodium phosphate, about 3% w/v sodium magnesium silicate, and about 3% w/v of a blend of dimethicone and cyclomethicone.

In some embodiments, the surface for sanitizing is skin. In some embodiments, the surface for sanitizing is a hand or hands of a subject. In some embodiments, the subject is an animal. In some embodiments, the subject is a mammal. In some embodiments, the subject is a human. In some embodiments, applying a sanitizing formulation to a surface includes killing at least one superbug.

In some embodiments, a superbug includes a microorganism that has developed a resistance or tolerance to a drug treatment. In some embodiments, the superbug includes *Staphylococcus aureus* (including methicillin-resistant *S. aureus* (MRSA) and vancomycin-resistant *S. aureus* (VRSA)), extended spectrum beta-lactamase (ESBL), *Pseudomonas aeruginosa, Clostridium difficile, Salmonella, Mycobacterium tuberculosis, Escherichia coli* (including Carbapenem resistant *E. coli*), multidrug-resistant *Acinetobacter baumannii* (MRAB), vancomycin-resistant *Enterococcus* (VRE), Carbapenem resistant *Klebsiella pneumoniae*, HIV, hepatitis, and influenza, or a combination thereof.

In some embodiments, the method includes providing the sanitizing formulation and applying the sanitizing formulation. In some embodiments, the sanitizing formulation is provided as a ready-to-use formulation that includes hypochlorite or acids or salts thereof, a silicone polymer or blend thereof, sodium phosphate, sodium magnesium silicate, and further may include hydrochloric acid, water, or buffer. In some embodiments, the sanitizing formulation is provided in portions, and further additions and/or mixing is required prior to use. In some embodiments, the sanitizing formulation is applied to a hand or hands of a subject. In some embodiments, the sanitizing formulation is applied on the surface of a device. In some embodiments, the sanitizing formulation is applied multiple times daily, once daily, multiple times weekly, once weekly, multiple times monthly, or once monthly, or within a time frame defined by any two of the aforementioned time frames. In some embodiments, the sanitizing formulation is applied liberally. In some embodiments, the sanitizing formulation is applied meagerly.

In some embodiments is provided a method of sanitizing hands. In some embodiments, the method includes applying to a user's hands a sanitizing formulation. In some embodiments, the sanitizing formulation is the formulation as described previously. In some embodiments, the sanitizing formulation includes hypochlorous acid, sodium phosphate, sodium magnesium silicate, and a silicone polymer or blend thereof. In some embodiments, the sanitizing formulation includes hypochlorous acid in an amount of about 75 ppm, sodium phosphate in an amount of about 0.2% w/v, sodium magnesium silicate in an amount of about 3% w/v, and a blend of dimethicone and cyclomethicone in an amount of about 3% w/v. In some embodiments, the sanitizing formulation includes water, hydrochloric acid, buffer, or combinations thereof.

In some embodiments, applying a sanitizing formulation to a user's hands includes killing at least one superbug. In some embodiments, a superbug includes a microorganism that has developed a resistance or tolerance to a drug treatment. In some embodiments, the superbug is at least one selected from the group consisting of *Staphylococcus aureus* (including methicillin-resistant *S. aureus* (MRSA) and vancomycin-resistant *S. aureus* (VRSA)), extended spectrum beta-lactamase (ESBL), *Pseudomonas aeruginosa, Clostridium difficile, Salmonella, Mycobacterium tuberculosis, Escherichia coli* (including Carbapenem resistant *E. coli*), multidrug-resistant *Acinetobacter baumannii* (MRAB), vancomycin-resistant *Enterococcus* (VRE), Carbapenem resistant *Klebsiella pneumoniae*, HIV, hepatitis, and influenza.

In some embodiments, the method includes providing the sanitizing formulation and applying the sanitizing formulation to a hand or hands of a subject. In some embodiments, the sanitizing formulation is provided as a ready-to-use formulation that includes hypochlorite or acids or salts thereof, a silicone polymer or blend thereof, sodium phosphate, sodium magnesium silicate, and further may include hydrochloric acid, water, or buffer. In some embodiments, the sanitizing formulation is provided in portions, and further additions and/or mixing is required prior to use. In some embodiments, the sanitizing formulation is applied on the surface of a device. In some embodiments, the sanitizing formulation is applied multiple times daily, once daily, multiple times weekly, once weekly, multiple times monthly, or once monthly, or within a time frame defined by any two of the aforementioned time frames. In some embodiments, the sanitizing formulation is applied liberally. In some embodiments, the sanitizing formulation is applied meagerly.

In some embodiments is provided a method of making a sanitizing formulation. In some embodiments, making a sanitizing formulation includes mixing a hypochlorite solution with a silicone polymer to form a sanitizing formulation.

DETAILED DESCRIPTION

It will be readily understood that the aspects of the present disclosure, as generally described herein, can be arranged, substituted, combined, separated, and designed in a wide variety of different configurations, all of which are explicitly contemplated herein.

Sanitizing compositions, including hand sanitizing compositions are described herein that are useful for disinfecting a surface, including skin and hands. In some embodiments is provided a method of sanitizing hands including applying the sanitizing solution as described herein to a user's hands. In some embodiments, the sanitizing composition may be used alone or in combination with other antibiotics or sanitizing solutions. In some embodiments, sanitizing solutions may be useful for disinfecting a surface to remove bacteria, viruses, yeasts, fungi, molds, and protozoa.

Definitions

Unless defined otherwise, technical and scientific terms used herein have the same meaning as commonly understood by one of ordinary skill in the art to which the present disclosure belongs. For purposes of the present disclosure, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In some embodiments, the "purity" of any given agent (for example, dimethicone or hypochlorous acid) in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by analytical chemistry techniques.

As used herein, the terms "function" and "functional" and the like refer to a biological, chemical, mechanical, or therapeutic function.

As used herein, the term "sanitizing composition" refers to a composition or formulation that is capable of disinfecting a surface. A sanitizing composition has anti-microbial properties, capable of removing microorganisms from a surface, and capable of preventing growth and proliferation of microorganisms on a surface. In some embodiments, the sanitizing composition is applied to a surface, such as a medical instrument or device, or to a biological surface. Biological surfaces include skin or hair of an animal, including, for example the skin or hair of a human. In some embodiments, the sanitizing composition is a hand sanitizer for use on the hands to destroy microorganisms or to prevent or inhibit the growth of microorganisms.

In some embodiments, microorganisms include superbugs, which are microorganisms that have developed a tolerance for or resistance to disinfecting agents, and are therefore not affected by anti-microbial treatments. In some embodiments, sanitizing compositions described herein are effective at inhibiting or preventing the growth of microorganisms on a surface, including preventing or inhibition the growth of superbugs. In some embodiments, administration of a sanitizing composition will kill one or more microorganisms or superbugs. In some embodiments, superbugs include, for example, *Staphylococcus aureus* (including methicillin-resistant *S. aureus* (MRSA) and vancomycin-resistant *S. aureus* (VRSA)), extended spectrum beta-lactamase (ESBL), *Pseudomonas aeruginosa, Clostridium difficile, Salmonella, Mycobacterium tuberculosis, Escherichia coli* (including Carbapenem resistant *E. coli*), multidrug-resistant *Acinetobacter baumannii* (MRAB), vancomycin-resistant *Enterococcus* (VRE), Carbapenem resistant *Klebsiella pneumoniae*, HIV, hepatitis, and influenza.

"Hypochlorous acid", as used herein, refers to a weak acid having the chemical formula HClO. Hypochlorous acid is also known as chloric (I) acid, chloranol, or hydroxidochlorine. Salts of hypochlorous acid are referred to herein as hypochlorites, and can include, for example, sodium hypochlorite (NaClO), calcium hypochlorite ($Ca(ClO)_2$), or potassium hypochlorite (KClO). It is intended that the term hypochlorite include the ion having the chemical formula $ClO^-$. As described herein, hypochlorous acid and hypochlorite are used as killing agents, skin cleansing agents, disinfectants, antibacterial agents, sanitizers, and/or preservatives. Hypochlorite, or acids and salts thereof, may be used in the sanitizing compositions of the present disclosure at an amount of about 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is about 25% w/v. In some embodiments, the hypochlorite salt or hypochlorous acid is added directly to a sanitizing composition. In some embodiments, the final amount of hypochlorite is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorite in the sanitizing composition is between about 50 to about 100 ppm. In some embodiments, the amount of hypochlorite in the sanitizing composition is about 75 ppm.

In some embodiments, the hypochlorite is added to the sanitizing composition as a hypochlorite solution. In some embodiments, the hypochlorite solution is prepared from hypochlorite salt or hypochlorous acid. In some embodiments, the solution of hypochlorite is prepared by passing a sodium chloride solution through electrolysis. In some embodiments, the sodium chloride solution is a 0.1%, 0.15%, 0.2%, 0.25%, 0.3%, 0.35%, 0.4% or greater w/v % or within a range defined by any two of the aforementioned amounts. In some embodiments, the sodium chloride is 0.28%, and the resulting hypochlorite solution is 300 ppm. In some embodiments, the hypochlorite solution is added to the sanitizing composition in an amount of about 0.5%, 1%, 5%, 10%, 15%, 20%, 25%, 30%, 40%, 50% or greater w/v %, or within a range defined by any two of the aforementioned amounts. In some embodiments, the solution includes, for example, about 300 ppm hypochlorite is added to a sanitizing composition in an amount of about 25% w/v.

As used herein, silicone polymers include dimethicone, which is also known as polydimethylsiloxane (PDMS), dimethylpolysiloxane, E900, or polymerized siloxane and has the chemical formula of $CH_3[Si(CH_3)_2O]_nSi(CH_3)_3$ where n is the number of repeating monomer $[Si(CH_3)_2]$ units. Silicone polymers also include cyclomethicone, which is a cyclic siloxane. The formulations described herein include blends of silicone polymers, including blends of dimethicone and cyclomethicone. Silicone polymers are used as an inert slip agent and increase the comfort of sanitizing compositions. The silicone polymer or blend of silicone polymers may be used in the sanitizing composition in an amount of about 0.5%, 1%, 1.5%, 2%, 2.5%, 3%, 3.5%, 4%, 4.5%, 5%, 10%, or 15%, or greater w/v %, or in an amount within any two of the aforementioned values or between a range defined by these values. In some embodiments, the amount of silicone polymer or a blend of silicone polymers is about 3% w/v. The blend of silicone polymers may include a ratio of dimethicone to cyclomethicone in an amount of about 1:5, 1:4, 1:3, 1:2, 1:1, 2:1, 3:1, 4:1, or 5:1, or within an amount defined by any two of the aforementioned ratios. In some embodiments, the ratio of dimethicone to cyclomethicone is about 1:1.

As used herein, the term "sodium magnesium silicate" refers to a silicate of sodium and magnesium and is a synthetic silicate clay, having magnesium and sodium silicate. It is used as a binder and bulking agent in cosmetics and personal care products, in part because of its ability to absorb water. Sodium magnesium silicate is effective in slowing the decomposition of formulas, and can prevent premature darkening of compositions and prevent premature development of a foul odor, thereby improving the shelf life of cosmetic compositions. In some embodiments, the sodium magnesium silicate is Laponite. As used herein, sodium magnesium silicate is useful as a gelling agent or rheology modifier. Thus, sodium magnesium silicate as used herein may have properties similar to an emulsifier. In some embodiments, the sodium magnesium silicate used herein may be considered an emulsifier. Sodium magnesium silicate may be used in the sanitizing composition in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of sodium magnesium silicate is about 3% w/v.

As used herein, the term "sodium phosphate monobasic" refers to the chemical formula of $NaH_2PO_4$, an inorganic compound of sodium with dihydrogen phosphate. Sodium phosphate monobasic may be referred to herein as sodium dihydrogen phosphate, sodium phosphate, monosodium phosphate, sodium biphosphate, acid sodium phosphate, monosodium orthophosphate, or primary sodium phosphate. As described herein, sodium phosphate monobasic may be used for adjustment of pH, as a thickening agent, or as a buffer. Sodium phosphate monobasic may be used in the sanitizing composition in an amount of about 0.05%, 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values. In some embodiments, the amount of sodium phosphate is about 0.2% w/v.

As used herein, the term "hydrochloric acid" refers to a chloric acid HCl. Hydrochloric acid may be added to the sanitizing composition to lower the pH. In some embodiments, HCl is added as a final step to decrease the pH. In some embodiments, HCl is used as a buffer. In some embodiments, HCl introduces ions, which causes the sanitizing composition to thicken as a result of excess ions. Thus, HCl is used in some embodiments as a thickener. Accordingly, in some embodiments is provided a sanitizing composition including hypochlorous acid, sodium phosphate, sodium magnesium silicate, dimethicone, and hydrochloric acid. Hydrochloric acid may be used in the sanitizing composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values. In some embodiments, the amount of HCl is about 0.08%.

As used herein, the pH of the formulation is the numerical scale to specify the acidity or basicity of the formulation. In some embodiments, the pH of the formulation is about 5.0, 5.5, 6.0, 6.5, 6.6, 6.7, 6.8, 6.9, 7.0, 7.1, 7.2, 7.3, 7.4, 7.5, 7.6, 7.7, 7.8, 7.9, 8.0, or 8.5, or within a ranged defined by any two of the aforementioned values. In some embodiments, the pH of the formulation is in a range from about 6.5 to about 7.8.

The sanitizing composition described herein may further include an additive known in the art can be included. Exemplary additives include emulsifiers, detergents, emollients, moisturizers, humectants, pigments, dyes, pearlescent compounds, nacreous pigments, bismuth oxychloride coated mica, titanium dioxide coated mica, colorants, fragrances, biocides, preservatives, alpha hydroxy acids, antioxidants, anti-microbial agents, anti-fungal agents, antiperspirant agents, exfoliants, hormones, enzymes, medicinal compounds, vitamins, salts, electrolytes, alcohols, polyols, polypropylene glycol, polyisobutene, polyoxyethylene, behenic acid, behenyl, sugar-alcohols, absorbing agents for ultraviolet radiation, botanical extracts, surfactants, silicone oils, organic oils, waxes, alkaline or acidic or buffering agents, film formers, thickening agents, hyaluronic acid, fumed silica, hydrated silica, talc, kaolin, starch, modified starch, mica, nylon, clay, bentonite, organo-modified clays and combinations thereof.

In some embodiments, the sanitizing composition described herein is characterized in having an osmolality by vapor pressure of about 10, 20, 30, 35, 36, 37, 38, 39, 40, 41, 42, 43, 44, 45, 46, 47, 48, 49, 50, 55, 60, 70, 80, 90, or 100 mmol/kg, or within a range defined by any two of the aforementioned amounts. In some embodiments, the osmolality by vapor pressure is about 38 mmol/kg. In some embodiments, the osmolality by vapor pressure is about 49 mmol/kg. In some embodiments, the sanitizing composition is characterized in having an osmolality by freezing point depression of about 10, 15, 20, 21, 22, 23, 24, 25, 26, 27, 28, 29, 30, 35, 40, 45, 50, 51, 52, 53, 54, 55, 56, 57, 58, 59, 60, 65, 70, 80, 90, or 100 mOsm/kg, or within a range defined by any two of the aforementioned amounts. In some embodiments, the osmolality by freezing point depression is about 22 mOsm/kg. In some embodiments, the osmolality by freezing point depression is about 54 mOsm/kg.

In some embodiments is provided a method of making the sanitizing composition formulation. In some embodiments, the method includes providing hypochlorite. In some embodiments, the hypochlorite is provided as a hypochlorite acid or salt. In some embodiments, the hypochlorite is provided as a hypochlorite solution. In some embodiments, the method of making the sanitizing composition includes providing hypochlorite in an amount of about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, hypochlorite is provided in an amount of about 50 to 100 ppm. In some embodiments, the hypochlorite is provided in an amount of about 75 ppm.

In some embodiments, the method of making the sanitizing composition includes providing a hypochlorite solution. In some embodiments, the hypochlorite solution is prepared from hypochlorite acids or salts. In some embodiments, the hypochlorite salt is sodium hypochlorite. In some embodiments, the hypochlorite solution is prepared from sodium chloride. In some embodiments, the method includes running sodium chloride solution through electrolysis. In some embodiments, the sodium chloride solution is provided in an amount of about 0.1%, 0.15%, 0.2%, 0.25%, 0.3%, 0.35%, or 0.4% w/v. In some embodiments, the sodium chloride is 0.28%, and the resulting hypochlorite solution is about 300 ppm. In some embodiments, the method of making the sanitizing composition includes diluting the hypochlorite solution to provide hypochlorite in an amount of about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, hypochlorite is provided in an amount of about 50 to 100 ppm. In some embodiments, the hypochlorite is provided in an amount of about 75 ppm.

In some embodiments, the method of making the sanitizing composition further includes providing a silicone polymer or a blend of silicone polymers. In some embodiments, the silicone polymer is a silicone polymer blend of dimethicone and cyclomethicone in a ratio of about 1:1. In some embodiments, the silicone polymer or blend thereof is provided in an amount of about 0.5%, 1%, 1.5%, 2%, 2.5%, 3%, 3.5%, 4%, 4.5%, 5%, 10%, or 15%, w/v, or within a range defined by any two of the aforementioned amounts. In some embodiments, the silicone polymer or blend thereof is provided in an amount of about 3% w/v.

In some embodiments, the method further includes providing sodium magnesium silicate. In some embodiments, the sodium magnesium silicate is provided in an amount of about 0.1%, 0.25%, 0.5%, 0.75%, 1%, 1.5%, 2%, 2.5%, 3%, 3.5%, 4%, 4.5%, 5%, 6%, 7%, 10%, or 15% w/v or within a range defined by any two of the aforementioned amounts. In some embodiments, the sodium magnesium silicate is provided in an amount of about 3% w/v.

In some embodiments, the method of making the sanitizing composition further includes providing sodium phosphate, HCl, water, or buffer or combinations thereof. In some embodiments, the sodium phosphate is provided in an amount of about 0.05%, 0.1%, 0.2%, 0.3%, 0.4%, 0.5%, 1%, 1.5%, 2%, or 2.5% w/v or within a range defined by any two of the aforementioned amounts. In some embodiments, sodium phosphate is provided in an amount of about 0.2% w/v.

In some embodiments, HCl may be used in the sanitizing composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values. In some embodiments, the amount of HCl is about 0.08%.

In some embodiments, the water and/or buffer is provided in an amount to make up the balance of the sanitizing composition, and is provided in an amount of about 20%, 30%, 40%, 45%, 50%, 55%, 56%, 57%, 58%, 59%, 60%, 61%, 61.55%, 62%, 62.5%, 63%, 65%, 70%, 75%, 80%, or 90% w/v or within a range defined by any two of the aforementioned amounts.

As used herein, the term "buffer" refers to a buffering agent and is used for balancing the pH and/or osmolality of the sanitizing composition. Examples of a buffer for use herein include, for example, salts of phosphates (such as sodium phosphate), borates, citrates, malates, formates, lactates, succinates, acetates, ascorbates, carbonates, bicarbonates, organic compound based buffers (including, for example, TRIS, HEPES, MOPS, MES, PIPES, TES, bicine, tricine, TAPSO), sodium ions, potassium ions, chloride ions (such as from HCl), bicarbonate ions, glucose, sucrose, peptides, proteins, a combination or mixture thereof or other agents that are chemically, functionally, or physiologically equivalent or similar. The sanitizing composition compositions provided herein have an optimum pH and viscosity, with an osmolality that is hypo-osmotic, having an osmolality by vapor pressure of about 10, 20, 30, 35, 36, 37, 38, 39, 40, 41, 42, 43, 44, 45, 46, 47, 48, 49, 50, 55, 60, 70, 80, 90, or 100 mmol/kg, or within a range defined by any two of the aforementioned amounts. In some embodiments, the osmolality by vapor pressure is about 38 mmol/kg. In some embodiments, the osmolality by vapor pressure is about 49 mmol/kg. In some embodiments, the sanitizing composition is characterized in having an osmolality by freezing point depression of about 10, 15, 20, 21, 22, 23, 24, 25, 26, 27, 28, 29, 30, 35, 40, 45, 50, 51, 52, 53, 54, 55, 56, 57, 58, 59, 60, 65, 70, 80, 90, or 100 mOsm/kg, or within a range defined by any two of the aforementioned amounts. In some embodiments, the osmolality by freezing point depression is about 22 mOsm/kg. In some embodiments, the osmolality by freezing point depression is about 54 mOsm/kg. The osmolality of the sanitizing composition can be determined by vapor pressure osmometry or freezing point osmometry.

In some embodiments is provided a method of using a sanitizing composition. In some embodiments, the method includes providing the sanitizing composition and applying the sanitizing composition. In some embodiments, the sanitizing composition is provided as a ready-to-use formulation that includes hypochlorite or acids or salts thereof, silicone polymer or a blend of silicone polymers, and sodium magnesium silicate, and further may include sodium phosphate, HCl, water, or buffer. In some embodiments, the sanitizing composition is provided in portions, and further additions and/or mixing is required prior to use. In some embodiments, the sanitizing composition is applied to the hands of a user. In some embodiments, the sanitizing composition is applied multiple times daily, once daily, multiple times weekly, once weekly, multiple times monthly, or once monthly, or within a time frame defined by any two of the aforementioned time frames. In some embodiments, the sanitizing composition is applied liberally. In some embodiments, the sanitizing composition is applied meagerly.

In some embodiments, the sanitizing composition as disclosed herein is useful for disinfecting a surface, including hands. In some embodiments, the sanitizing composition described herein is used in a healthcare facility setting. In some embodiments, the sanitizing composition includes hypochlorite, or a salt or acid thereof, a blend of dimethicone and cyclomethicone, and sodium magnesium silicate. In some embodiments, the sanitizing composition includes water and/or buffer, hypochlorous acid solution, a blend of dimethicone and cyclomethicone, sodium magnesium silicate, sodium phosphate, and HCl.

In some embodiments is provided a method of using a sanitizing composition for eliminating microbial causing infections. In some embodiments, the sanitizing composition provided herein is capable of destroying or preventing superbug infections. In some embodiments, the sanitizing compositions destroy or prevent infections of *Staphylococcus aureus* (including methicillin-resistant *S. aureus* (MRSA) and vancomycin-resistant *S. aureus* (VRSA)), extended spectrum beta-lactamase (ESBL), *Pseudomonas aeruginosa, Clostridium difficile, Salmonella, Mycobacterium tuberculosis, Escherichia coli* (including Carbapenem resistant *E. coli*), multidrug-resistant *Acinetobacter baumannii* (MRAB), vancomycin-resistant *Enterococcus* (VRE), Carbapenem resistant *Klebsiella pneumoniae*, HIV, hepatitis, and influenza. In embodiments, administration of a sanitizing composition will kill one or more superbugs.

In some embodiments is provided a method of using the sanitizing composition to stop a fungal infection. In some embodiments, the fungal infection is caused by a yeast of the *Candida* genus. In one embodiment, the yeast is of the *Candida albicans* species. In other embodiments, the *Candida* yeast may be of the *Candida dubliniensis, Candida parapsilosis, Candida tropicalis, Candida kerfyr, Candida guilliermondii, Candida inconspicua, Candida famata, Candida glabrata, Candida krusei, Candida lusitaniae*, or other *Candida* species, or combinations thereof. In some embodiments, the sanitizing composition is used to stop a viral infection.

In some embodiments, the sanitizing composition as disclosed herein is useful as a hand sanitizer or as a medical or surgical disinfectant for use with medical instruments for disinfecting a medical device or instrument prior to, during, or after use. In some embodiments, the sanitizing composition is useful for disinfecting counter tops and table tops. In some embodiments, the sanitizing compositions are useful for disinfecting items found in areas of public use, such as hand rails, benches, or other items that may be prone to frequent public use, and which may harbor microbial colonies.

In some embodiments, the sanitizing composition as disclosed herein is useful for sanitizing a surface without causing damage or harm to the surface. Some commonly used sanitizing compositions, including alcohol-based compositions, are known to adversely break down the finish of a surface, such as a wax or shine of a floor. However, the compositions described herein advantageously do not degrade the finish of a surface, including the wax or shine of a floor.

The invention is generally disclosed herein using affirmative language to describe the numerous embodiments. The invention also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention as it is described herein above and/or in the claims.

Example 1

Preparation of Sanitizing Compositions

The following example demonstrates the method of preparing the sanitizing composition and various compositions or formulations thereof.

A sanitizing composition was prepared with the ingredients as provided in Table 1. Hypochlorite or a salt or acid thereof was added to water, a blend of dimethicone and cyclomethicone, sodium magnesium silicate, and sodium phosphate in the preparation of a sanitizing composition.

TABLE 1

Sanitizing Composition

| Ingredient | Quantity |
| --- | --- |
| Water and/or buffer | balance |
| Hypochlorite | 75 ppm |
| Dimethicone and Cyclomethicone Blend | 3% w/v |
| Sodium Magnesium Silicate | 3% w/v |
| Sodium Phosphate | 0.2% w/v |

The sanitizing composition formulation described in Table 1 is useful inhibiting, eradicating, or reducing an organismal population. Various microbial pathogens may be inhibited or reduced, including *Staphylococcus aureus* (including methicillin-resistant *S. aureus* (MRSA) and vancomycin-resistant *S. aureus* (VRSA)), extended spectrum beta-lactamase (ESBL), *Pseudomonas aeruginosa, Clostridium difficile, Salmonella, Mycobacterium tuberculosis, Escherichia coli* (including Carbapenem resistant *E. coli*), multidrug-resistant *Acinetobacter baumannii* (MRAB), vancomycin-resistant *Enterococcus* (VRE), Carbapenem resistant *Klebsiella pneumoniae*, HIV, hepatitis, and influenza.

Alternative Preparation Example 1

A sanitizing composition having 25% of a 220 ppm hypochlorite solution was added to 3% w/v of a blend of dimethicone and cyclomethicone, with 3% w/v sodium magnesium silicate and 0.2% sodium phosphate, with the balance water. The hypochlorite solution was prepared by passing 0.28% sodium chloride through electrolysis to provide a 220 ppm hypochlorite solution. The composition was thickened by adding hydrochloric acid in an amount of 0.05% w/v.

In another alternative composition, the ingredients are identical to those shown in Table 1, but sodium phosphate is replaced with 0.08% w/v hydrochloric acid, as shown in Table 2.

TABLE 2

Alternative Composition

| Ingredient | Quantity |
| --- | --- |
| Water and/or buffer | balance |
| Hypochlorite | 75 ppm |
| Dimethicone and Cyclomethicone Blend | 3% w/v |
| Sodium Magnesium Silicate | 3% w/v |
| Hydrochloric Acid | 0.08% w/v |

Example 2

Time Kill Assay for Antimicrobial Agents

The following example demonstrates the efficacy of some embodiments of the sanitizer as described herein.

A sanitizing composition was used to determine the efficacy as an antimicrobial agent against a variety of microbes. The composition was prepared as described in Example 1, and was exposed to the microbes for various lengths of time. Test microbes were obtained from the American Type Culture Collection (ATCC; Manassas, Va.), Centers for Disease Control and Prevention (CDC; Atlanta, Ga.), and the NARSA Contracts Administrator at Focus Technologies, Inc. (Herndon, Va.).

Bacteria were grown in tryptic soy agar+5% sheep's blood at 35-37° C. in aerobic conditions. The neutralizer for the bacteria was Letheen broth+0.1% sodium thiosulfate. *Candida albicans* was grown in Sabouraud dextrose agar at 25-30° C. in aerobic conditions. The neutralizer for *C. albicans* was Sabouraud dextrose broth+0.1% sodium thiosulfate. A suspension of the test organism was exposed to the sanitizing composition for the specified exposure time (15, 30, 60, or 120 seconds) at ambient temperature (20° C.). Each test was performed in replicate. After exposure, an aliquot of the suspension was transferred to a neutralizer and was assayed for survivors. Appropriate culture purity, neutralizer sterility, test population, and neutralization confirmation controls were performed. Table 3 provides the raw data for the number of survivors (in colony forming units, CFU) at each exposure time and at dilutions of $10^0$ (1.00 mL), $10^0$ (0.100 mL), $10^{-1}$ (0.100 mL), $10^{-2}$ (0.100 mL), and $10^{-3}$ (0.100 mL).

TABLE 3

Time Kill Test Results

| Test Organism | Dilution (Volume Plated) | Exposure Time (seconds) Number of Survivors (CFU) | | | |
|---|---|---|---|---|---|
| | | 15 | 30 | 60 | 120 |
| Multi-drug Resistant *Acinetobacter baumannii* (MRAB; ATCC 19606) | $10^0$ (1.00 mL) | T, T | 0, 0 | 0, 0 | 0, 0 |
| | $10^0$ (0.100 mL) | 63, 52 | 0, 0 | 0, 0 | 0, 0 |
| | $10^{-1}$ (0.100 mL) | 7, 5 | 0, 0 | 0, 0 | 0, 0 |
| | $10^{-2}$ (0.100 mL) | 3, 2 | 0, 0 | 0, 0 | 0, 0 |
| | $10^{-3}$ (0.100 mL) | 0, 0 | 0, 0 | 0, 0 | 0, 0 |
| *Candida albicans* (ATCC 10231) | $10^0$ (1.00 mL) | T, T | T, T | T, T | T, T |
| | $10^0$ (0.100 mL) | T, T | T, T | T, T | T, T |
| | $10^{-1}$ (0.100 mL) | 179, 120 | 120, 134 | T, T | T, T |
| | $10^{-2}$ (0.100 mL) | 23, 18 | 24, 30 | 33, 35 | 38, 33 |
| | $10^{-3}$ (0.100 mL) | 5, 6 | 1, 5 | 2, 5 | 11, 4 |
| Vancomycin Resistant *Enterococcus faecalis* (VRE; ATCC 51299) | $10^0$ (1.00 mL) | T, T | 216, 250 | 0, 0 | 0, 0 |
| | $10^0$ (0.100 mL) | T, T | 21, 20 | 0, 0 | 0, 0 |
| | $10^{-1}$ (0.100 mL) | 52, 61 | 6, 1 | 0, 0 | 0, 0 |
| | $10^{-2}$ (0.100 mL) | 12, 13 | 0, 0 | 0, 0 | 0, 0 |
| | $10^{-3}$ (0.100 mL) | 1, 0 | 0, 0 | 0, 0 | 0, 0 |
| *Escherichia coli* (ATCC 11229) | $10^0$ (1.00 mL) | 0, 0 | 0, 0 | 0, 0 | 0, 0 |
| | $10^0$ (0.100 mL) | 0, 0 | 0, 0 | 0, 0 | 0, 0 |
| | $10^{-1}$ (0.100 mL) | 0, 0 | 1, 2 | 0, 0 | 0, 0 |
| | $10^{-2}$ (0.100 mL) | 3, 1 | 0, 0 | 0, 0 | 0, 0 |
| | $10^{-3}$ (0.100 mL) | 0, 0 | 0, 0 | 0, 0 | 0, 0 |

TABLE 3-continued

Time Kill Test Results

| Test Organism | Dilution (Volume Plated) | Exposure Time (seconds) Number of Survivors (CFU) | | | |
|---|---|---|---|---|---|
| | | 15 | 30 | 60 | 120 |
| Carbapenem Resistant *Escherichia coli* (CDC 81371) | $10^0$ (1.00 mL) | T, T | 83, 61 | 0, 0 | 0, 0 |
| | $10^0$ (0.100 mL) | T, T | 7, 7 | 0, 0 | 0, 0 |
| | $10^{-1}$ (0.100 mL) | 40, 39 | 0, 3 | 0, 0 | 0, 0 |
| | $10^{-2}$ (0.100 mL) | 6, 2 | 0, 0 | 0, 0 | 0, 0 |
| | $10^{-3}$ (0.100 mL) | 0, 0 | 0, 0 | 0, 0 | 0, 0 |
| Extended-Spectrum beta-lactamase (ESBL) producing *Escherichia coli* (ATCC BAA-196) | $10^0$ (1.00 mL) | T, T | 0, 0 | 0, 0 | 0, 0 |
| | $10^0$ (0.100 mL) | 43, 46 | 0, 0 | 0, 0 | 0, 0 |
| | $10^{-1}$ (0.100 mL) | 5, 6 | 0, 0 | 0, 0 | 0, 0 |
| | $10^{-2}$ (0.100 mL) | 0, 0 | 0, 0 | 0, 0 | 0, 0 |
| | $10^{-3}$ (0.100 mL) | 0, 0 | 0, 0 | 0, 0 | 0, 0 |
| Carbapenem Resistant *Klebsiella pneumoniae* (ATCC BAA-1705) | $10^0$ (1.00 mL) | 164, 112 | 0, 0 | T, T | 0, 0 |
| | $10^0$ (0.100 mL) | 15, 12 | 0, 0 | 82, 54 | 0, 0 |
| | $10^{-1}$ (0.100 mL) | 0, 1 | 0, 0 | 10, 18 | 0, 0 |
| | $10^{-2}$ (0.100 mL) | 0, 0 | 0, 0 | 0, 1 | 0, 0 |
| | $10^{-3}$ (0.100 mL) | 0, 0 | 0, 0 | 0, 2 | 0, 0 |
| *Pseudomonas aeruginosa* (ATCC 15442) | $10^0$ (1.00 mL) | 92, 152 | 0, 0 | 0, 0 | 0, 0 |
| | $10^0$ (0.100 mL) | 11, 6 | 0, 0 | 0, 0 | 0, 0 |
| | $10^{-1}$ (0.100 mL) | 2, 1 | 0, 0 | 0, 0 | 0, 0 |
| | $10^{-2}$ (0.100 mL) | 0, 0 | 0, 0 | 0, 0 | 0, 0 |
| | $10^{-3}$ (0.100 mL) | 0, 0 | 0, 0 | 0, 0 | 0, 0 |
| *Salmonella enterica* (ATCC 10708) | $10^0$ (1.00 mL) | 142, 122 | 0, 0 | 0, 0 | 0, 0 |
| | $10^0$ (0.100 mL) | 12, 14 | 0, 0 | 0, 0 | 0, 0 |
| | $10^{-1}$ (0.100 mL) | 0, 1 | 0, 0 | 0, 0 | 0, 0 |
| | $10^{-2}$ (0.100 mL) | 0, 1 | 0, 0 | 0, 0 | 0, 0 |
| | $10^{-3}$ (0.100 mL) | 0, 0 | 0, 0 | 0, 0 | 0, 0 |
| *Staphylococcus aureus* (ATCC 6538) | $10^0$ (1.00 mL) | 18, 17 | 0, 0 | 0, 0 | 0, 0 |
| | $10^0$ (0.100 mL) | 3, 5 | 0, 0 | 0, 0 | 0, 0 |
| | $10^{-1}$ (0.100 mL) | 0, 0 | 0, 0 | 0, 0 | 0, 0 |
| | $10^{-2}$ (0.100 mL) | 0, 0 | 0, 0 | 0, 0 | 0, 0 |
| | $10^{-3}$ (0.100 mL) | 0, 0 | 0, 0 | 0, 0 | 0, 0 |
| Methicillin Resistant *Staphylococcus aureus* (MRSA; ATCC 33592) | $10^0$ (1.00 mL) | T, T | 0, 0 | 0, 0 | 0, 0 |
| | $10^0$ (0.100 mL) | T, T | 0, 0 | 0, 0 | 0, 0 |
| | $10^{-1}$ (0.100 mL) | 96, 78 | 0, 0 | 0, 0 | 0, 0 |
| | $10^{-2}$ (0.100 mL) | 13, 13 | 0, 0 | 0, 0 | 0, 0 |
| | $10^{-3}$ (0.100 mL) | 2, 0 | 0, 0 | 0, 0 | 0, 0 |
| Vancomycin Resistant *Staphylococcus aureus* (VRSA; NARSA VRS1) | $10^0$ (1.00 mL) | T, T | 4, 1 | 0, 0 | 0, 0 |
| | $10^0$ (0.100 mL) | T, T | 0, 0 | 0, 0 | 0, 0 |
| | $10^{-1}$ (0.100 mL) | 93, 68 | 0, 0 | 0, 0 | 0, 0 |
| | $10^{-2}$ (0.100 mL) | 15, 14 | 0, 0 | 0, 0 | 0, 0 |
| | $10^{-3}$ (0.100 mL) | 1, 1 | 0, 0 | 0, 0 | 0, 0 |

T = Too numerous to count (>300 colonies)
CFU = Colony Forming Units

The raw data presented in Table 3 was used to calculate the percent reduction and $Log_{10}$ survivors, and is presented in Table 4. A value of <1 was used in place of zero for calculation purposes. The data presented below shows a percent reduction of bacterial populations in the tested bacteria ranging from about 95.4% to greater than about 99.9% at 15 seconds, from about 99.8% to greater than about 99.999% at 30 seconds, from about 99.8% to greater than about 99.999% at 60 seconds, and greater than about 99.999% at 120 seconds.

TABLE 4

Calculated Survival of Time Kill Assay

| Test Organism | Exposure Time (seconds) | CFU/mL in Test Population Control ($Log_{10}$) | CFU/mL of Survivors | $Log_{10}$ Survivors | Percent Reduction | $Log_{10}$ Reduction |
|---|---|---|---|---|---|---|
| Multi-drug Resistant *Acinetobacter baumannii* (MRAB; ATCC 19606) | 15 | $3.2 \times 10^6$ (6.51) | $5.8 \times 10^3$ | 3.76 | 99.8% | 2.75 |
| | 30 | | <5 | <0.70 | >99.999% | >5.81 |
| | 60 | | <5 | <0.70 | >99.999% | >5.81 |
| | 120 | | <5 | <0.70 | >99.999% | >5.81 |

TABLE 4-continued

Calculated Survival of Time Kill Assay

| Test Organism | Exposure Time (seconds) | CFU/mL in Test Population Control ($Log_{10}$) | CFU/mL of Survivors | $Log_{10}$ Survivors | Percent Reduction | $Log_{10}$ Reduction |
|---|---|---|---|---|---|---|
| *Candida albicans* | 15 | $1.57 \times 10^5$ | $1.50 \times 10^5$ | 5.18 | 4.46% | 0.02 |
| (ATCC 10231) | 30 | (5.20) | $1.27 \times 10^5$ | 5.10 | 19.1% | 0.10 |
| | 60 | | $3.4 \times 10^5$ | 5.53 | No reduction | No reduction |
| | 120 | | $3.6 \times 10^5$ | 5.56 | No reduction | No reduction |
| Vancomycin Resistant | 15 | $2.02 \times 10^6$ | $5.7 \times 10^4$ | 4.76 | 97.2% | 1.55 |
| *Enterococcus faecalis* | 30 | (6.31) | $2.33 \times 10^3$ | 3.37 | >99.8% | 2.94 |
| (VRE; ATCC 51299) | 60 | | <5 | <0.70 | >99.999% | >5.61 |
| | 120 | | <5 | <0.70 | >99.999% | >5.61 |
| *Escherichia coli* | 15 | $3.2 \times 10^6$ | $2 \times 10^4$ | 4.30 | 99.4% | 2.21 |
| (ATCC 11229) | 30 | (6.51) | $2 \times 10^3$ | 3.30 | 99.9% | 3.21 |
| | 60 | | <5 | <0.70 | >99.999% | >5.81 |
| | 120 | | <5 | <0.70 | >99.999% | >5.81 |
| Carbapenem Resistant | 15 | $1.99 \times 10^6$ | $4.0 \times 10^4$ | 4.60 | 98.0% | 1.70 |
| *Escherichia coli* (CDC | 30 | (6.30) | $7.2 \times 10^2$ | 2.86 | >99.9% | 3.44 |
| 81371) | 60 | | <5 | <0.70 | >99.999% | >5.60 |
| | 120 | | <5 | <0.70 | >99.999% | >5.60 |
| Extended-Spectrum | 15 | $1.09 \times 10^6$ | $4.5 \times 10^3$ | 3.65 | 99.6% | 2.39 |
| beta-lactamase (ESBL) | 30 | (6.04) | <5 | <0.70 | >99.999% | >5.34 |
| producing *Escherichia* | 60 | | <5 | <0.70 | >99.999% | >5.34 |
| *coli* (ATCC BAA-196) | 120 | | <5 | <0.70 | >99.999% | >5.34 |
| Carbapenem Resistant | 15 | $3.3 \times 10^6$ | $1.38 \times 10^3$ | 3.14 | >99.9% | 3.38 |
| *Klebsiella pneumoniae* | 30 | (6.52) | <5 | <0.70 | >99.999% | >5.82 |
| (ATCC BAA-1705) | 60 | | $6.8 \times 10^3$ | 3.83 | 99.8% | 2.69 |
| | 120 | | <5 | <0.70 | >99.999% | >5.82 |
| *Pseudomonas* | 15 | $1.27 \times 10^6$ | $1.22 \times 10^3$ | 3.09 | 99.9% | 3.01 |
| *aeruginosa* (ATCC | 30 | (6.10) | <5 | <0.70 | >99.999% | >5.40 |
| 15442) | 60 | | <5 | <0.70 | >99.999% | >5.40 |
| | 120 | | <5 | <0.70 | >99.999% | >5.40 |
| *Salmonella enterica* | 15 | $1.55 \times 10^6$ | $1.32 \times 10^3$ | 3.12 | 99.9% | 3.07 |
| (ATCC 10708) | 30 | (6.19) | <5 | <0.70 | >99.999% | >5.49 |
| | 60 | | <5 | <0.70 | >99.999% | >5.49 |
| | 120 | | <5 | <0.70 | >99.999% | >5.49 |
| *Staphylococcus aureus* | 15 | $2.81 \times 10^6$ | $1.8 \times 10^2$ | 2.26 | 99.99% | 4.19 |
| (ATCC 6538) | 30 | (6.45) | <5 | <0.70 | >99.999% | >5.75 |
| | 60 | | <5 | <0.70 | >99.999% | >5.75 |
| | 120 | | <5 | <0.70 | >99.999% | >5.75 |
| Methicillin Resistant | 15 | $4.8 \times 10^6$ | $8.7 \times 10^4$ | 4.94 | 98.2% | 1.74 |
| *Staphylococcus aureus* | 30 | (6.68) | <5 | <0.70 | >99.999% | >5.98 |
| (MRSA; ATCC 33592) | 60 | | <5 | <0.70 | >99.999% | >5.98 |
| | 120 | | <5 | <0.70 | >99.999% | >5.98 |
| Vancomycin Resistant | 15 | $1.78 \times 10^6$ | $8.1 \times 10^4$ | 4.91 | 95.4% | 1.34 |
| *Staphylococcus aureus* | 30 | (6.25) | $3 \times 10^1$ | 1.48 | >99.99% | 4.77 |
| (VRSA; NARSA | 60 | | <5 | <0.70 | >99.999% | >5.55 |
| VRS1) | 120 | | <5 | <0.70 | >99.999% | >5.55 |

The data presented in Example 2 indicates the potent antimicrobial properties of the sanitizing compositions provided in some embodiments herein, and shows that the composition is useful for the inhibition, eradication, and reduction of microbial populations.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of sanitizing hands, comprising:
    applying to a user's hands a sanitizing formulation comprising:
        hypochlorite present in an amount of about 10 to about 200 ppm;
        sodium magnesium silicate present in an amount of about 0.5 to about 5% w/v;
        a silicone polymer or blend thereof present in an amount of about 0.5 to about 5% w/v; and
        sodium phosphate present in an amount of about 0.05 to about 5% w/v or hydrochloric acid present in an amount of about 0.01 to about 1% w/v,
        the sanitizing formulation having a pH of about 6.5 to about 8.5.

2. The method of claim 1, wherein hypochlorite is in an amount of about 75 ppm, wherein the sodium phosphate is in an amount of about 0.2% w/v, wherein the hydrochloric acid is present in an amount of about 0.08% w/v, wherein the sodium magnesium silicate is in an amount of about 3% w/v, and wherein the silicone polymer or blend thereof is in an amount of about 3% w/v.

3. The method of claim 1, wherein the sanitizing formulation further comprises water, buffer, or combinations thereof.

4. The method of claim 1, wherein sanitizing hands comprises inhibiting growth of at least one superbug on the user's hands.

5. The method of claim 4, wherein the superbug is at least one selected from the group comprising *Staphylococcus aureus* (including methicillin-resistant *S. aureus* (MRSA) and vancomycin-resistant *S. aureus* (VRSA)), extended spectrum beta-lactamase (ESBL), *Pseudomonas aeruginosa, Clostridium difficile, Salmonella, Mycobacterium tuberculosis, Escherichia coli* (including Carbapenem resistant *E. coli*), multidrug-resistant *Acinetobacter baumannii* (MRAB), vancomycin-resistant *Enterococcus* (VRE), Carbapenem resistant *Klebsiella pneumoniae*, HIV, hepatitis, and influenza.

6. The method of claim 1, wherein the pH is about 6.5 to about 7.5.

7. The method of claim 1, wherein the sanitizing composition is applied at least once a day.

8. The method of claim 1, wherein sanitizing hands the method further comprises treating a fungal infection on the user's hands.

9. The method of claim 8, wherein the fungal infection is a yeast of the *Candida* genus.

10. The method of claim 9, wherein the fungal infection is at least one selected from the group comprising *Candida albicans, Candida dubliniensis, Candida parapsilosis, Candida tropicalis, Candida kerfyr, Candida guilliermondii, Candida inconspicua, Candida famata, Candida glabrata*, and *Candida kruse*.

11. The method of claim 1, wherein sanitizing hands comprises treating a viral infection on the user's hands.

* * * * *